US012042394B2

(12) United States Patent
Noshchenko et al.

(10) Patent No.: US 12,042,394 B2
(45) Date of Patent: Jul. 23, 2024

(54) PATIENT-SPECIFIC SPINAL IMPLANTS

(71) Applicant: THE REGENTS OF THE UNIVERSITY OF COLORADO, A BODY CORPORATE, Denver, CO (US)

(72) Inventors: Andriy G. Noshchenko, Denver, CO (US); Evalina Burger-(Van Der Walt), Greenwood Village, CO (US); Vikas V. Patel, Denver, CO (US); Christopher J. Kleck, Englewood, CO (US); Ji Ma, Charlottesville, VA (US)

(73) Assignee: The Regents of The University of Colorado, A Body Corporate, Denver, CO (US)

( * ) Notice: Subject to any disclaimer, the term of this patent is extended or adjusted under 35 U.S.C. 154(b) by 379 days.

(21) Appl. No.: 17/266,535

(22) PCT Filed: Aug. 8, 2019

(86) PCT No.: PCT/US2019/045776
§ 371 (c)(1),
(2) Date: Feb. 5, 2021

(87) PCT Pub. No.: WO2020/033743
PCT Pub. Date: Feb. 13, 2020

(65) Prior Publication Data
US 2021/0315706 A1    Oct. 14, 2021

Related U.S. Application Data

(60) Provisional application No. 62/716,192, filed on Aug. 8, 2018.

(51) Int. Cl.
*A61F 2/44* (2006.01)
*A61F 2/30* (2006.01)

(52) U.S. Cl.
CPC .......... *A61F 2/442* (2013.01); *A61F 2/30942* (2013.01); *A61F 2002/30014* (2013.01);
(Continued)

(58) Field of Classification Search
CPC .... A61F 2/44; A61F 2/442; A61F 2/30; A61F 2/30942
See application file for complete search history.

(56) References Cited

U.S. PATENT DOCUMENTS

| | | | |
|---|---|---|---|
| 4,309,777 A * | 1/1982 | Patil | A61F 2/442 606/907 |
| 6,113,638 A * | 9/2000 | Williams | A61F 2/4455 606/279 |
| 6,261,293 B1 | 7/2001 | Nicholson et al. | |
| 7,174,282 B2 | 2/2007 | Hollister et al. | |
| 7,563,286 B2 * | 7/2009 | Gerber | A61F 2/4425 623/17.14 |

(Continued)

FOREIGN PATENT DOCUMENTS

| | | |
|---|---|---|
| CN | 204468348 | 7/2015 |
| CN | 105748177 | 7/2016 |

(Continued)

OTHER PUBLICATIONS

International Search Report and Written Opinion dated Dec. 4, 2019 in Application No. PCT/US2019/045776.

*Primary Examiner* — Christopher J Beccia
(74) *Attorney, Agent, or Firm* — Snell & Wilmer L.L.P.

(57) ABSTRACT

A spinal implant device comprising a frame and a plurality of mechanical stiffness members extending from the frame, with the plurality of mechanical stiffness members being individually customized to provide a specific axial stiffness. The plurality of mechanical stiffness members may be coupled to the frame, and the plurality of mechanical stiffness members may be a plurality of wave-spring modules. A (Continued)

method of treating spinal disease includes determining actual spatial mechanical properties across a vertebral contact surface of a vertebra of a patient. The method may also include manufacturing a spinal implant device that has conforming spatial mechanical properties that are specific to the patient and that are based on the actual spatial mechanical properties of the vertebral contact surface. The method may include surgically implanting the spinal implant device against the vertebral contact surface such that the actual spatial mechanical properties and the conforming spatial mechanical properties align.

18 Claims, 9 Drawing Sheets

(52) U.S. Cl.
CPC ............... *A61F 2002/3092* (2013.01); *A61F 2002/3093* (2013.01); *A61F 2002/30948* (2013.01)

(56) References Cited

U.S. PATENT DOCUMENTS

| | | | |
|---|---|---|---|
| 10,292,770 | B2 | 5/2019 | Ryan et al. |
| 2012/0215261 | A1 | 8/2012 | Massoudi |
| 2014/0035061 | A1 | 11/2014 | Aggarwal et al. |
| 2014/0350614 | A1 | 11/2014 | Frey et al. |
| 2017/0020262 | A1 | 1/2017 | May et al. |
| 2017/0143502 | A1* | 5/2017 | Yadin ............... A61F 2/442 |
| 2017/0202622 | A1 | 7/2017 | Park et al. |
| 2017/0036056 | A1 | 12/2017 | Tomellini |
| 2017/0360563 | A1 | 12/2017 | Hunt et al. |
| 2020/0390564 | A1* | 12/2020 | Wallenstein ............ A61F 2/447 |

FOREIGN PATENT DOCUMENTS

| | | |
|---|---|---|
| CN | 106344221 | 1/2017 |
| CN | 107252373 | 10/2017 |
| WO | 2004016217 | 2/2004 |
| WO | 2017223162 | 12/2017 |

\* cited by examiner

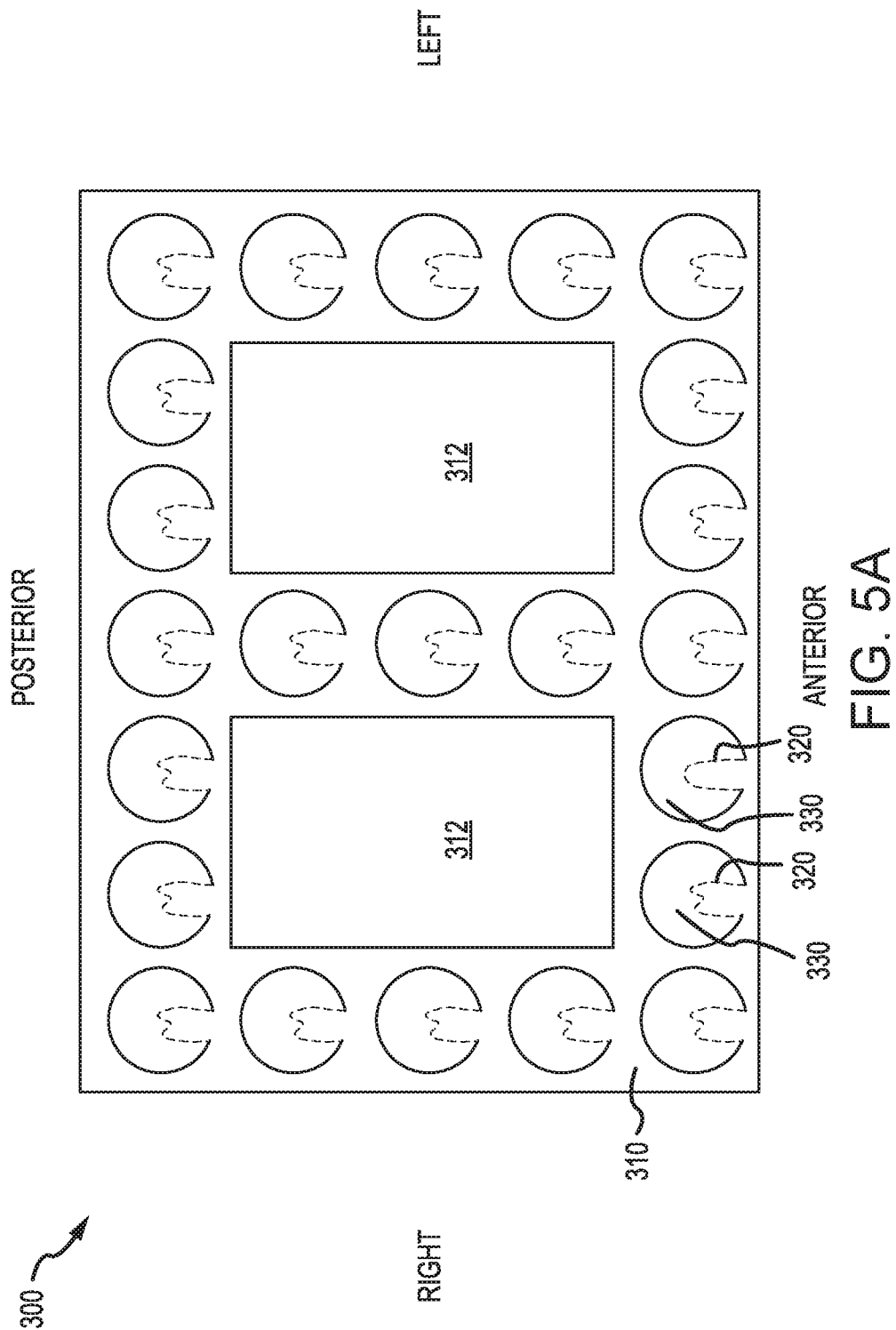

PATIENT-SPECIFIC SPINAL IMPLANTS

CROSS REFERENCE TO RELATED APPLICATIONS

This application is a U.S. national stage entry under 35 U.S.C. § 371 of International Application No. PCT/US2019/045776 filed Aug. 8, 2019 entitled "PATIENT-SPECIFIC SPINAL IMPLANTS", which claims priority to, and the benefit of, U.S. Provisional Patent Application Ser. No. 62/716,192, filed on Aug. 8, 2018, the entire contents of which are incorporated herein by reference in their entirety.

FIELD

The present disclosure relates to spinal implants, and more specifically to methods, systems, and devices for patient-specific spinal implants.

BACKGROUND

Currently, fusion is widely used for surgical treatment of different diseases, including degenerative disc disease, spinal deformity, spinal trauma, malignancies, etc. Spinal implants used in spinal fusion surgeries are commonly referred to as spine interbody devices. In conventional fusion procedures, spine implants are often used to restore intervertebral spacing and physiological curvatures of the spine. Further, spine implants can be used to replace damaged intervertebral disks and can be used to act both as a spacer and a scaffold to stabilize the spine to reduce patient discomfort due to misalignment and abnormal motion of vertebrae segments, degenerated or damaged disks, or pinched nerves. Spinal cages are also utilized in replacing a complete vertebral segment including the bone and both discs adjacent to the vertebral body.

Conventional implants, such as interbody cages and machined bone grafts, are often made of solid or porous material, such as titanium, polyetheretherketone, or cortical bone, and generally have mechanical stiffness and mechanical strength properties that exceed the corresponding mechanical properties of the vertebral contact surfaces. Due to this mismatch in mechanical properties between the implant and the endplates of the vertebrae, the implant may sink into the endplates of the vertebrae weeks to months after surgery, which is a condition known as subsidence. Moreover, conventional the implant designs do not take into account the uneven structure and nonhomogeneous distribution of mechanical properties across the vertebral contact surface. That is, because the mechanical property of such implants, which is determined by the mechanical properties of the material from which the implant is made, is not matched to the strength of the bone against which it is to be installed, an uneven distribution of the load across the vertebral surfaces results, which increases the risk of vertebral injury as well as implant subsidence, which often nullifies the intended benefits of the implant/fusion surgery. While revision surgery may be used address the problem of subsidence, the success rate of revision surgery decreases with each additional revision.

SUMMARY

In various embodiments, the present disclosure provides a method for treating spinal disease. The method includes determining actual spatial mechanical properties across a vertebral contact surface of a vertebra of a patient. The method also includes manufacturing a spinal implant device that has conforming spatial mechanical properties that are specific to the patient and that are based on the actual spatial mechanical properties of the vertebral contact surface. Finally, the method may also include surgically implanting the spinal implant device against the vertebral contact surface such that the actual spatial mechanical properties and the conforming spatial mechanical properties align.

In various embodiments, manufacturing the spinal implant device comprises forming a plurality of individual, discrete surface sections of the spinal implant device, with each discrete surface section of the plurality of discrete surface sections having specific mechanical properties that conform to mechanical properties of a corresponding surface section the vertebral contact surface against which the spinal implant device is to be installed. Forming the plurality of individual, discrete surface sections may include coupling a plurality of mechanical stiffness members to a frame, wherein each mechanical stiffness member of the plurality of mechanical stiffness members is individually customized to have a specific axial stiffness that matches the corresponding surface section of the vertebral contact surface against which it is implanted.

In various embodiments, determining the actual spatial mechanical properties of the vertebral contact surface comprises utilizing computed tomography to determine at least one of size, shape, and distribution of the actual spatial mechanical properties. Determining the actual spatial mechanical properties of the vertebral contact surface may include determining stiffness across the vertebral contact surface. Determining the actual spatial mechanical properties of the vertebral contact surface comprises mapping the vertebral contact surface with a grid or other coordinate system and mapping mechanical properties of each region of the grid. In various embodiments, determining the actual spatial mechanical properties of the vertebral contact surface comprises determining threshold levels of stress/load for region of the grid of the vertebral contact surface.

Also disclosed herein, according to various embodiments, is a spinal implant device comprising a frame and a plurality of mechanical stiffness members extending from the frame, with the plurality of mechanical stiffness members being individually customized to provide a specific axial stiffness, according to various embodiments.

In various embodiments, the plurality of mechanical stiffness members are coupled to the frame. In various embodiments, the plurality of mechanical stiffness members is a plurality of wave-spring modules. Each wave-spring module of the plurality of wave-spring modules may include a top plate, a bottom plate, and a spiral body disposed between the top plate and the bottom plate. In various embodiments, the plurality of mechanical stiffness members comprise surface caps. An outer surface of the surface caps may have a convex shape. In various embodiments, the surface caps are porous. In various embodiments, the frame defines through-holes for bone cell ingrowth. In various embodiments, the plurality of mechanical stiffness members are pedicles.

The forgoing features and elements may be combined in various combinations without exclusivity, unless otherwise expressly indicated herein. These features and elements, as well as the operation of the disclosed embodiments, will become more apparent in light of the following description and accompanying drawings.

BRIEF DESCRIPTION OF THE DRAWINGS

FIG. 5A is a coronal projection of a spinal implant device, in accordance with various embodiments;

Figure 1:
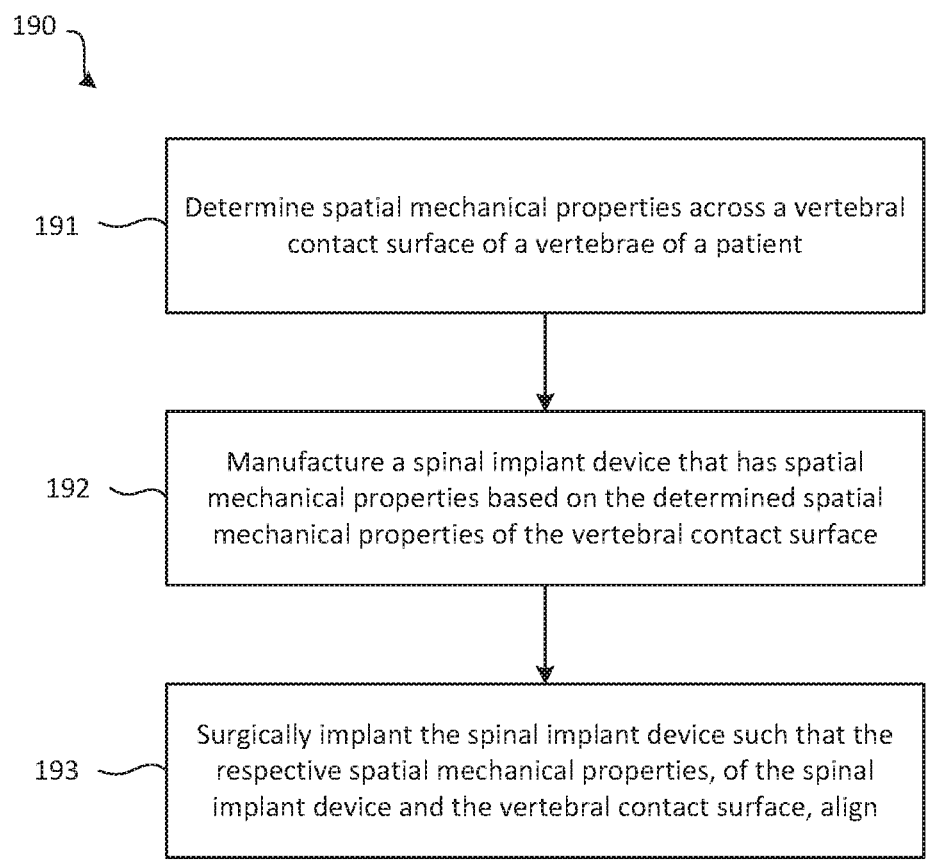
FIG. 1 is a schematic flow chart diagram of a method for treating spinal disease, in accordance with various embodiments.

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

DETAILED DESCRIPTION

The detailed description of exemplary embodiments herein makes reference to the accompanying drawings, which show exemplary embodiments by way of illustration. While these exemplary embodiments are described in sufficient detail to enable those skilled in the art to practice the disclosure, it should be understood that other embodiments may be realized and that logical changes and adaptations in design and construction may be made in accordance with this disclosure and the teachings herein without departing from the spirit and scope of the disclosure. Thus, the detailed description herein is presented for purposes of illustration only and not of limitation.

Disclosed herein, according to various embodiments, are methods, systems, and/or devices for spinal implants that have customized spatial mechanical properties that are specific to and that correspond with spatial mechanical properties of the vertebral contact surface against which the implant is configured to be installed. That is, the present disclosure generally relates to spinal implant devices, such as interbody cages for spinal arthrodesis (fusion), and their associated method(s) of design, manufacture, and installation. Generally, the spinal implant devices disclosed herein are specifically tailored to individual patients, thereby minimizing/reducing the risk of subsidence and other vertebral contact surface injuries.

In various embodiments, and with reference to FIG. 1, a method 190 of treating spinal disease is provided. The method 190 generally includes, according to various embodiments, determining spatial mechanical properties across a vertebral contact surface of a vertebra of a patient where an implant is configured to be surgically installed at step 191. The method 190 further includes manufacturing a spinal implant device that has spatial mechanical properties that are specific to the patient and based on the determined spatial mechanical properties of the vertebral contact surface at step 192, according to various embodiments. Further, the method 190 also includes, according to various embodiments, surgically implanting the spinal implant device against the vertebral contact surface such that the respective spatial mechanical properties of the implant and the vertebral contact surface are aligned at step 193. Accordingly, this treatment method 190 is generally a method of manufacturing a spinal implant device that has a plurality of individual, discrete surface sections, with each discrete surface section having customized mechanical properties that match a corresponding surface section of the vertebral contact surface against which the implant will be installed.

In various embodiments, and with continued reference to FIG. 1, the method 190 reduces the risk of post-operative injury of the vertebral surface and subsidence of conventional implants by creating a spinal implant device that has a spatial surface structure that is tailored to accommodate the mechanical properties and structure of the vertebral contact surface (also referred to herein as endplate) of the vertebra where the device will be implanted. In various embodiments, step 191 of the method 190 includes utilizing computed tomography to determine the size, shape, and distribution of the mechanical properties, such as stiffness, of the various regions of interest of the vertebral contact surface(s) of the vertebra of a patient. For example, step 191 of the method 190 may include mapping the location where the spinal implant device will be installed to determine the mechanical properties of the location. In various embodiments, for example, the vertebral contact surface may be mapped with a grid or other coordinate system, and the mechanical properties of each site/region in the grid may be determined. Determining the spatially varying mechanical properties of the multiple sites of the vertebral contact surface may include stress/strain tests using micro-CT and/or conventional CT technologies. The measured strain may be used to determine the bone density and/or stiffness of the localized site. These determined mechanical properties are indicative of the strength of superficial bone structure of the vertebra at discrete sites. In various embodiments, step 191 includes determining threshold levels of stress/load for each discrete site of the vertebral contact surface to prevent subsidence of the spinal implant device.

Figure 2:
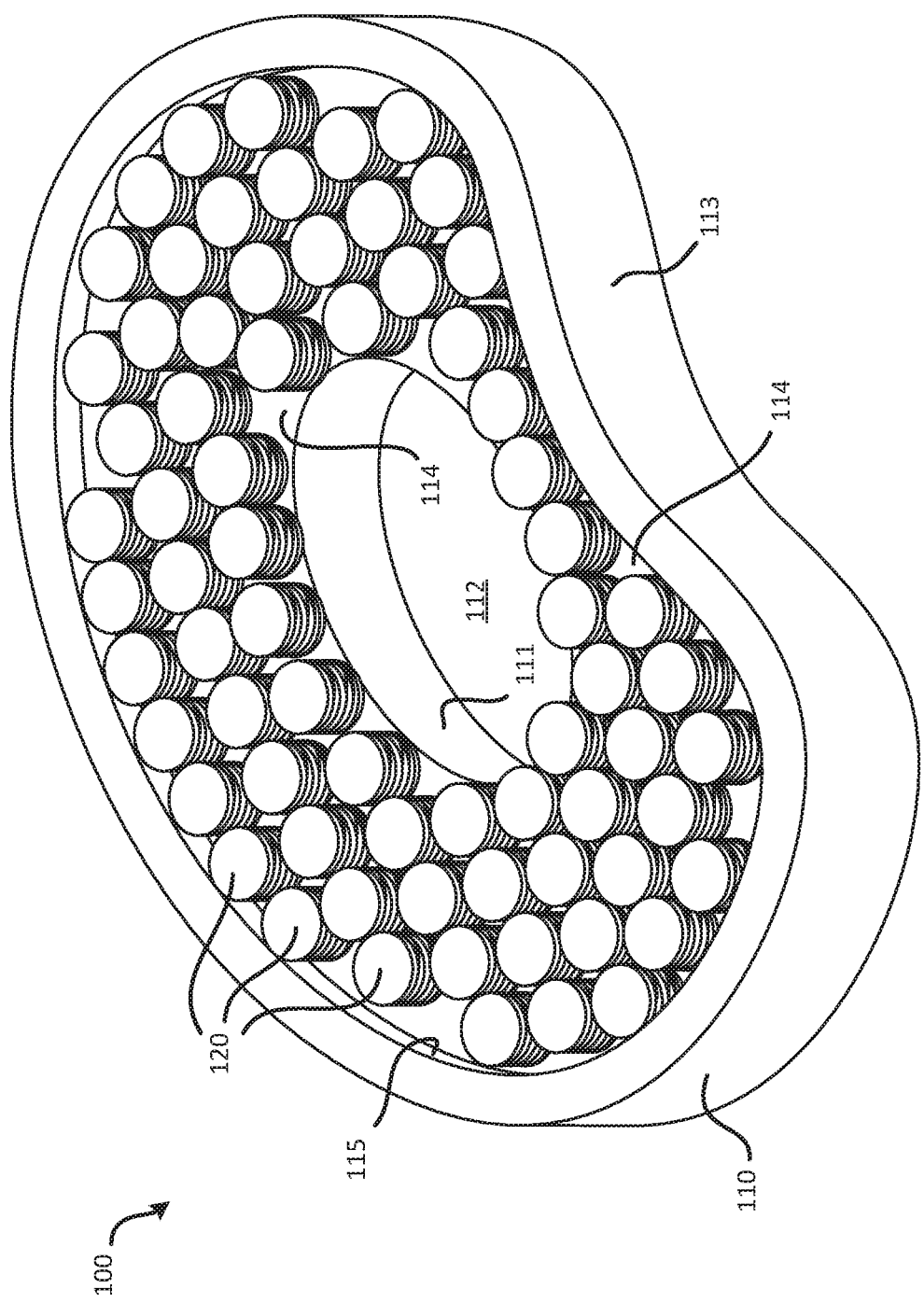
FIG. 2 is a perspective view of a spinal implant device comprising a frame and a plurality of mechanical stiffness members, in accordance with various embodiments.

In various embodiments, step 192 of the method 190 includes manufacturing a spinal implant device that has discrete regions with individualized mechanical properties that conform to the corresponding mechanical properties (e.g., the threshold levels of stress/load) of the mapped vertebral contact surface. In various embodiments, and with reference to FIG. 2, the spinal implant device 100 includes a frame 110 and a plurality of mechanical stiffness members 120 extending from the frame 110. The plurality of mechanical stiffness members 120 are individually customized to provide a specific axial stiffness. That is, as mentioned above, the plurality of mechanical stiffness members 120 have individual mechanical properties and are positioned across the frame 110 to align with the determined/actual spatial mechanical properties of the vertebral contact surface of a vertebra of a patient. That is, certain regions/areas of the vertebra of a patient may have lower hardness or stiffness properties than others, and thus the spinal implant device 100 may be manufactured to position mechanical stiffness members that have lower stiffness in such regions/areas.

In various embodiments, the frame 110 of the spinal implant device 100 is generally the base or structure to which the plurality of mechanical stiffness members 120 are coupled. For example, the plurality of mechanical stiffness members 120 may be coupled to a tray 114 of the frame 110 of the spinal implant device 100. In various embodiments, the plurality of mechanical stiffness members 120 are individually and separately manufactured and subsequently attached/mounted to the frame 110. However, the plurality of mechanical stiffness members 120 may be formed as extensions of the frame 110, for example using additive manufacturing methods, as described in greater detail below. The frame 110 of the spinal implant device 100 may have an inner periphery 111 that defines a through-hole 112. The through-hole 112 may facilitate bone cell ingrowth. The frame 110 may also have an outer periphery 113. The shape and size of the frame 110 (e.g., the shape of the inner periphery 111 and/or the outer periphery 113) may be customized to be specific to the patient.

In various embodiments, the frame 110 also includes a lip 115 extending around the tray 114 and providing a border for the tray 114. In addition to retaining the mechanical stiffness members 120 using an adhesive or other bonding agent, retention of the mechanical stiffness members 120 may be facilitated by the lip 115. That is, the lip 115 may prevent the mechanical stiffness members 120 from being liberated from the frame 110 and/or may prevent the mechanical stiffness members 120 from moving across the surface of the tray 114.

In addition to customizing the spatial stiffness of the device 100 using the individual and discrete mechanical stiffness members 120, the spinal implant device 100 may also be customized to have a topography (i.e., a relative elevation of the mechanical stiffness members 120) that matches/contours the contact surface of the vertebra against which the spinal implant device 100 is configured to be implanted. The customized topography of the spinal implant device 100 may be achieved via a tray 114 comprising an undulating (i.e., non-planar) surface, thereby imparting axial non-uniformity to the spinal implant device 100 to enable the device to better contour the contact surface of the vertebra against which the device is to be implanted. Alternatively or additionally, the height of the individual mechanical stiffness members 120 may be customized/tailored.

In various embodiments, and as described in greater detail below, the mechanical stiffness members 120 may include surface caps, with each surface cap being coupled to a respective mechanical stiffness and configured to engage specific regions/sites of the mapped vertebral contact surface in order to prevent excess load being transferred to the vertebra, thereby reducing the likelihood of subsidence. Accordingly, the customized shape (e.g. elevation of the tray 114), the individualized axial stiffness of the mechanical stiffness members 120, and the shape/design of any optional surface caps provide the spinal implant device 100 with spatially specific mechanical load responses, thereby enabling the spinal implant device 100 to mimic the spatial stiffness of the bone (vertebral contact surface) against which it is in contact after being surgically installed.

Figure 3A:
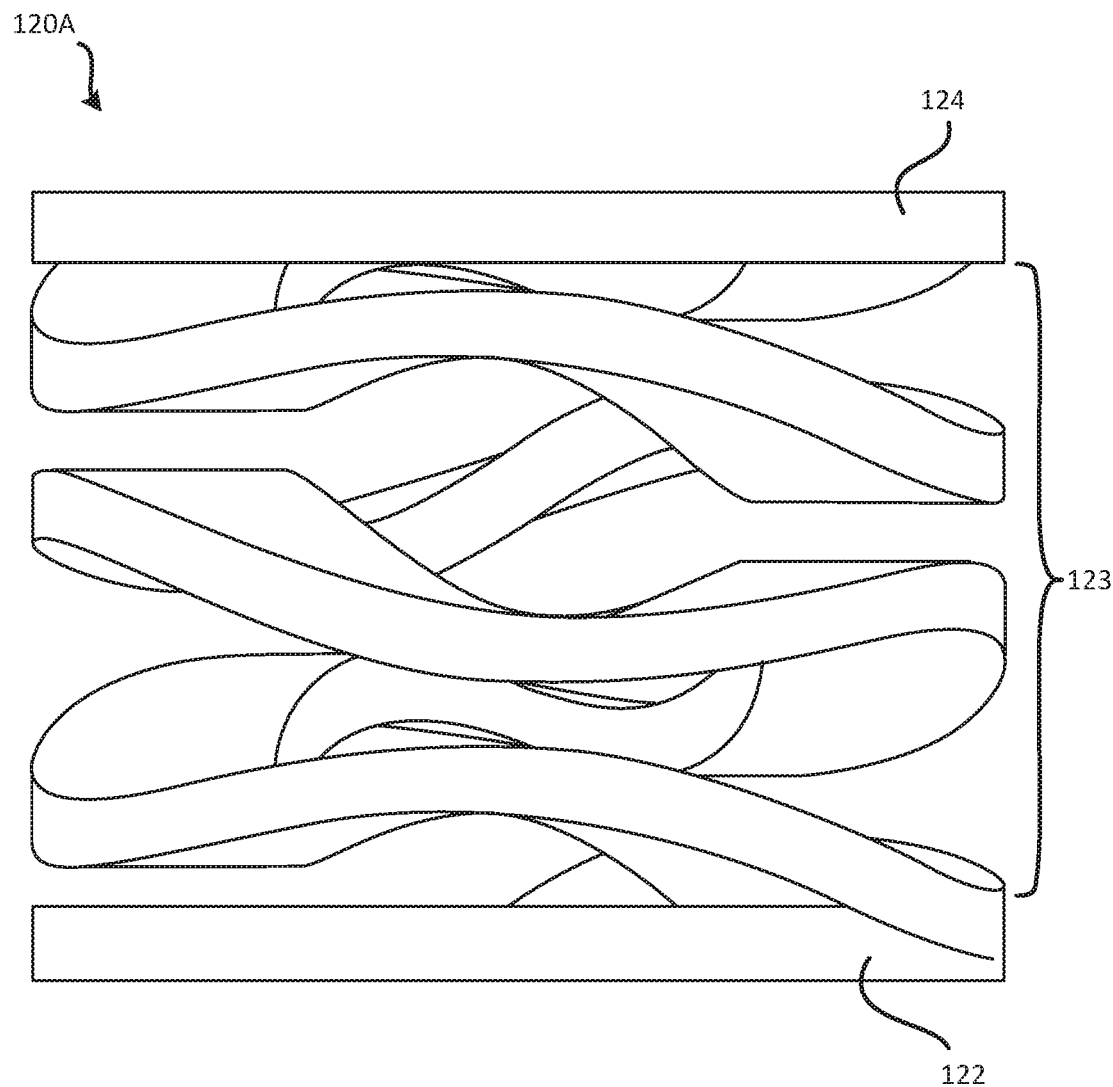
FIG. 3A is a side view of a wave-spring module as a mechanical stiffness member, in accordance with various embodiments.

In various embodiments, and with reference to FIG. 3A, the plurality of mechanical stiffness members is a plurality of wave-spring modules 120A. Each wave-spring module 120A may include a bottom plate 122, a top plate 124, and a spiral body 123 disposed between the bottom plate 122 and the top plate 124. The wave-spring modules 120A may be manufactured from a metal material, or may be manufactured from a resiliently deformable plastic or composite material. In various embodiments, the spiral body 123 provides the customized axial stiffness, and the bottom and top plates 122, 124 are for engaging the tray 114 and vertebra, respectively. The axial stiffness of the wave-spring module 120A may be customized based on the amplitude of the spiral body 123, the number of revolutions of the spiral body 123 between the plates 122, 124, the vertical/axial spacing between turns, and/or the thickness of the sections forming the spiral body 123.

In various embodiments, each wave-spring module 120A has a diameter of about 4 millimeters and a height of 2.5 millimeters. In various embodiments, the axial stiffness of each wave-spring module 120A is customized to have a stiffness of between about 50 Newtons per millimeter and about 400 Newtons per millimeter. In various embodiments, the axial stiffness of each wave-spring module 120A is customized to have a stiffness of between about 65 Newtons per millimeter and 330 Newtons per millimeter.

Figure 3B:
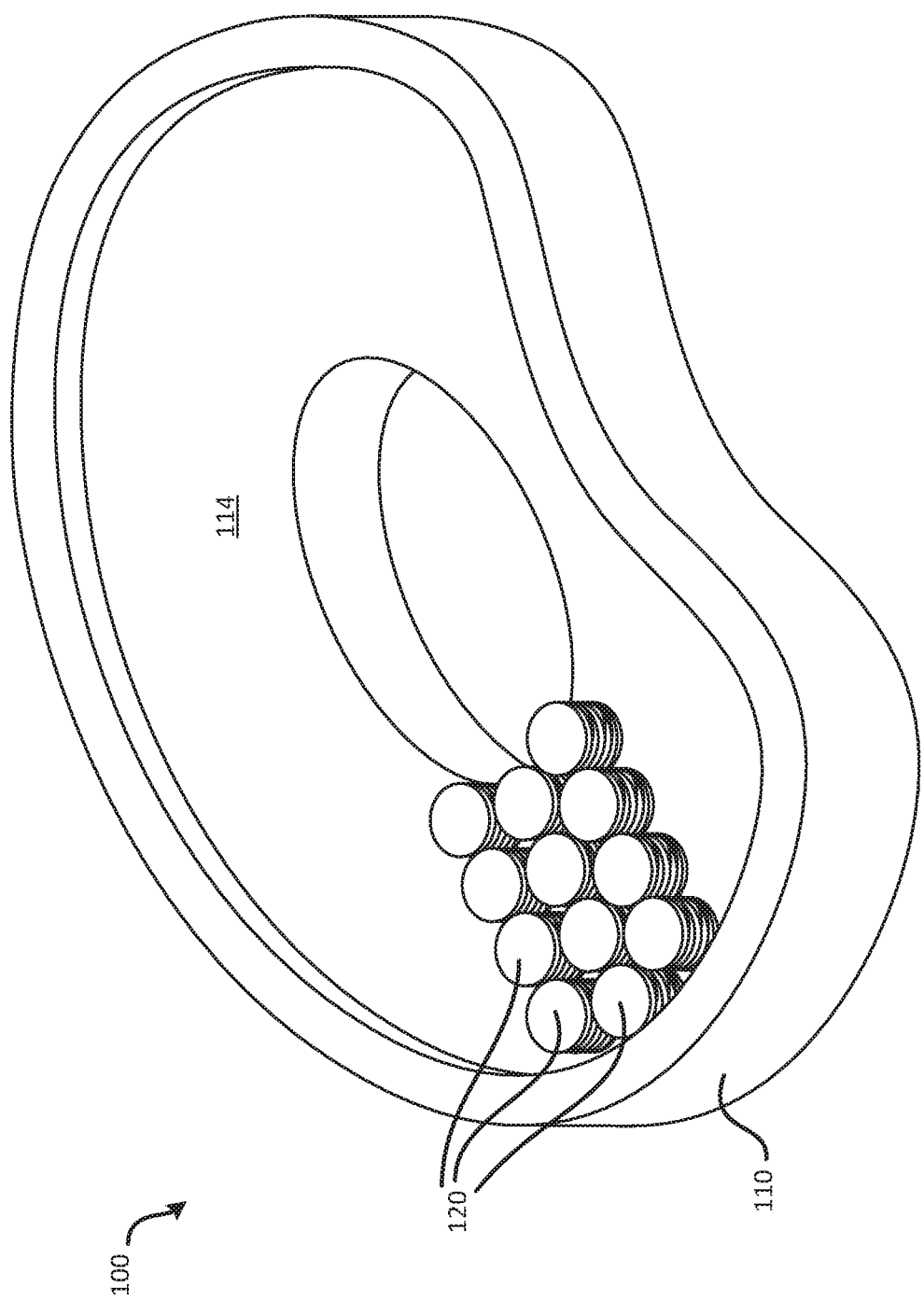
FIG. 3B is a perspective view of a spinal implant device in a partially assembled state, in accordance with various embodiments.

FIG. 3B shows a spinal implant device 100 in a partially assembled state. That is, as mentioned above, the method of manufacturing the spinal implant device 100 may include manufacturing individual mechanical stiffness members 120 and coupling them to the frame 110 of the device 100.

Figure 4A:
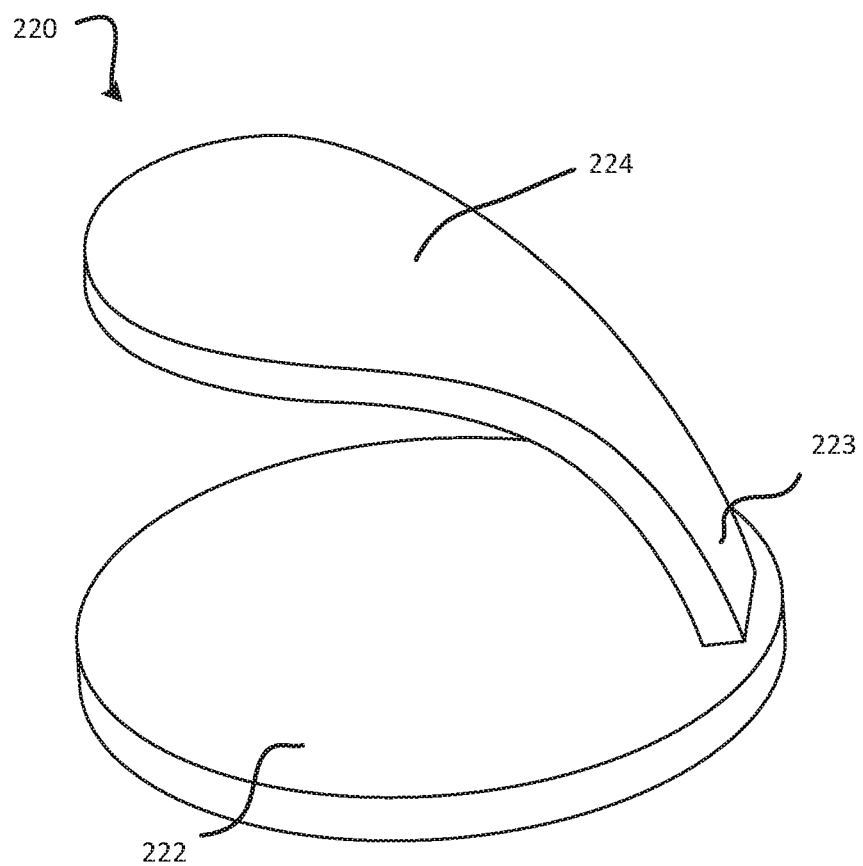
FIG. 4A is a perspective view of a mechanical stiffness member having a pedestal, in accordance with various embodiments.
Figure 4B:
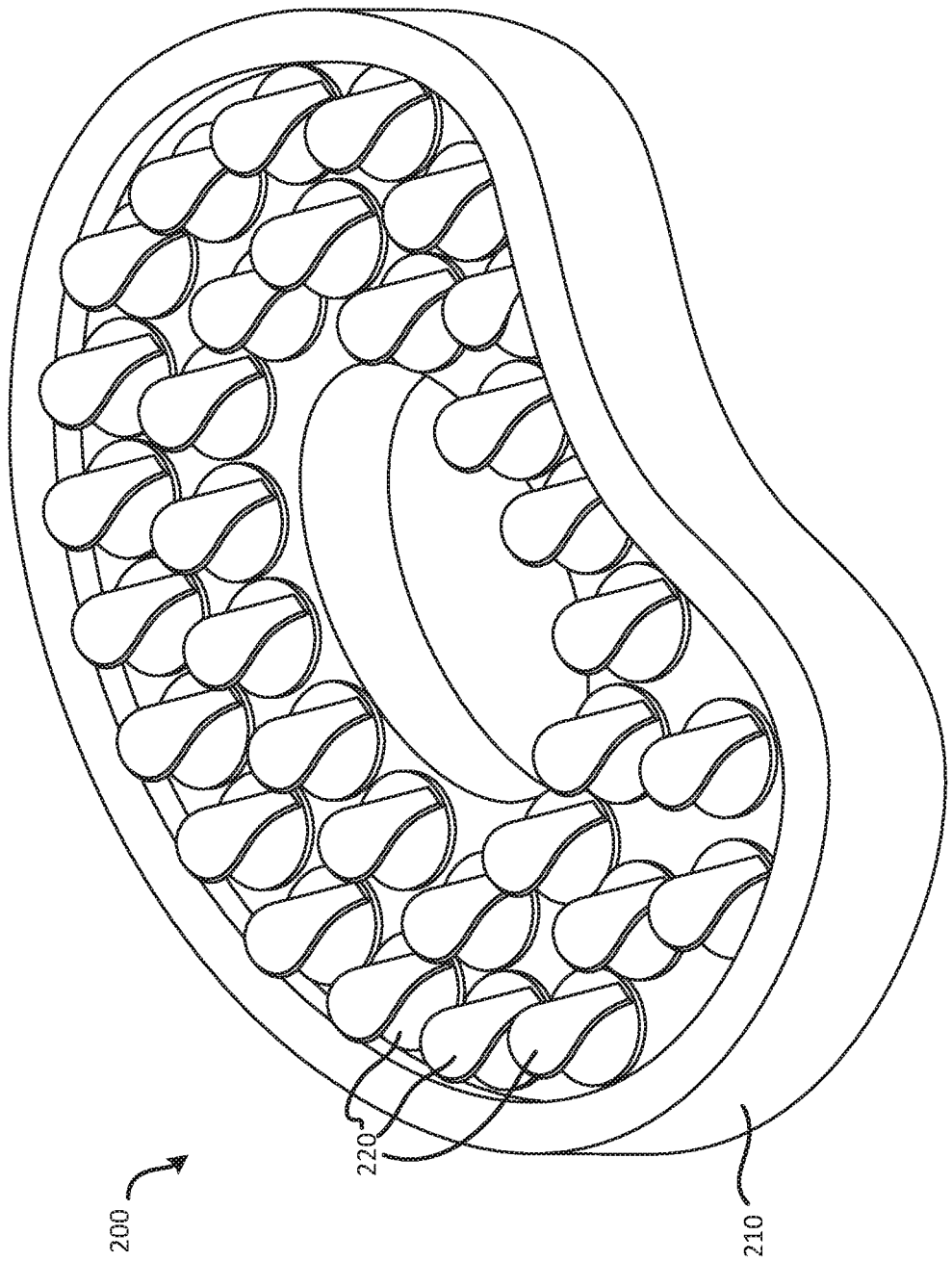
FIG. 4B is a perspective view of a spinal implant device having the pedestal mechanical stiffness members of FIG. 4A, in accordance with various embodiments.

In various embodiments, and with reference to FIGS. 4A and 4B, the mechanical stiffness members are pedestal spring modules 220. That is, the mechanical stiffness members may have a base 222 and a pedestal feature 224 extending from the base 222. Similar to the pedicles described below, the pedestal spring modules 220 may be manufactured from a resiliently deformable material that. The axial stiffness of the pedestal spring module 220 may be based on the dimensions, shape, and/or design of the neck 223 extending between the base 222 and the pedestal feature 224. In various embodiments, the orientation of the pedestal features 224 relative to other pedestal spring modules 220 of the plurality of pedestal spring modules may all be in the same direction, as shown in FIG. 4B, or the pedestal features 224 may be oriented in different directions to further customize and control the stiffness response of the spinal implant device 200.

Figure 5B:
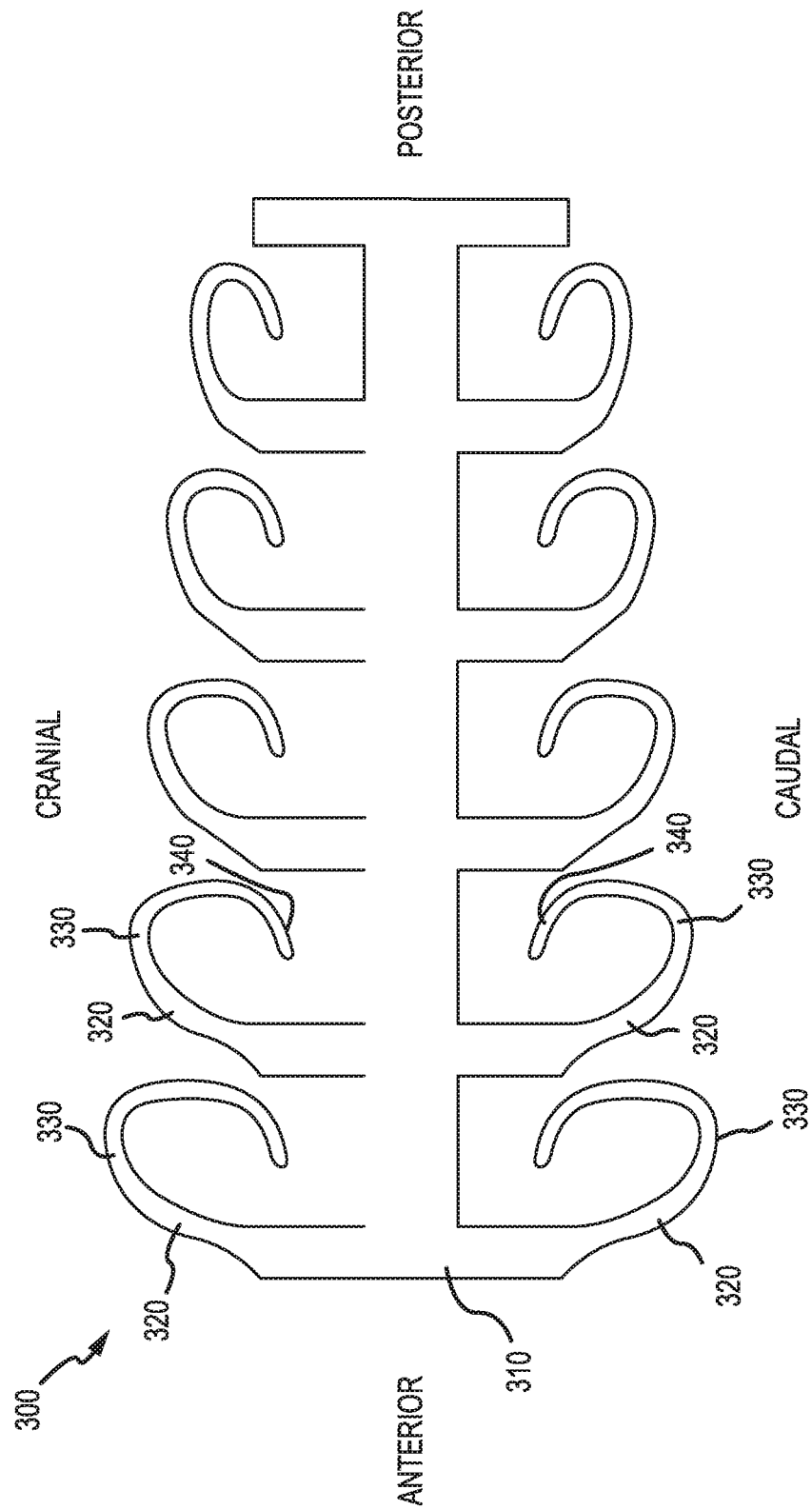
FIG. 5B is a sagittal projection of a spinal implant device, in accordance with various embodiments.

In various embodiments, and with reference FIGS. 5A and 5B, the spinal implant device 300 may have a rigid frame 310, and the plurality of mechanical stiffness members may be pedicles 320 that extend from the frame 310. The plurality of surface caps 330 may be coupled to/extend from the pedicles 320. In various embodiments, each of the pedicles 320 may be specifically designed and manufactured to provide a desired axial movement of its associated surface cap 330 in response to load. Accordingly, each of the pedicles 320 may have a specifically tailored thickness (e.g. transverse or sagittal thickness), may be made from a specifically tailored material, and/or may be otherwise individually modified to provide a desired deflection response.

The plurality of surface caps 330 may have a rounded shape. That is, the outer surface of these surface caps 330 may be convex, according to various embodiments, and this outer surface of the surface caps 330 may be configured to directly engage the discrete, mapped sites of the vertebral contact surface. Also, the plurality of surface caps 330 may be made from a porous material, which may facilitate bone cell ingrowth. In various embodiments, the frame 310 may define through-holes 312 that also allow for bone cell ingrowth, thereby facilitating spinal arthrodesis (fusion). Further, the spinal implant device 300 may include structural features 340 that limit the axial movement of the surface caps 330. For example, each of the surface caps 330 may have an internal/lower lip/edge that is specifically positioned a distance away from the frame 310, thereby limiting axial movement of the surface caps.

Figure 6:
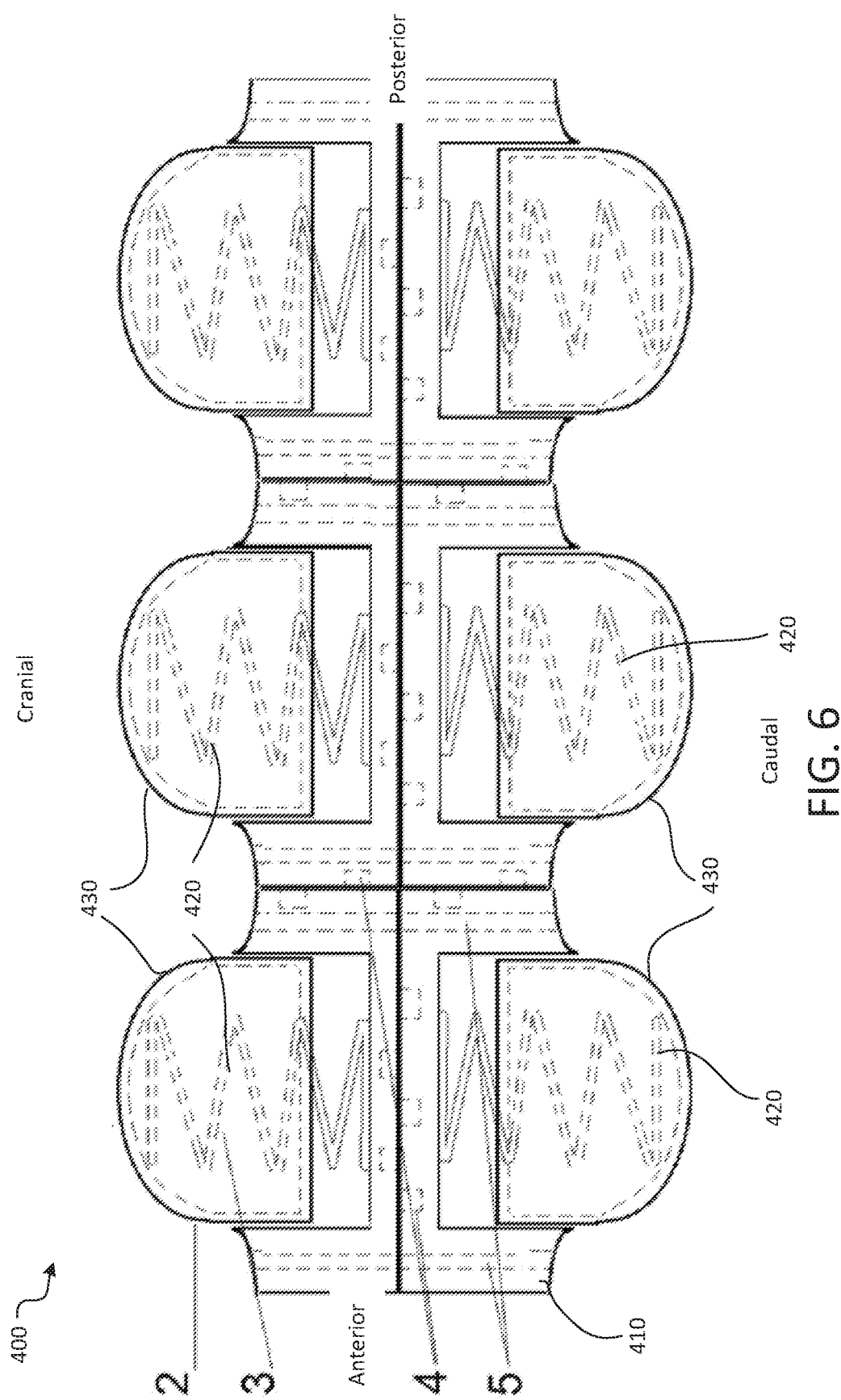
FIG. 6 is a sagittal projection of a portion of a spinal implant device, in accordance with various embodiments.

In various embodiments, and with reference to FIG. 6, another implementation of the spinal implant device 400 is provided. The spinal implant device 400 includes a frame 410, a plurality of springs 420 functioning as the mechanical stiffness members, and a plurality of surface caps 430. Similar to the pedicles 320 described above, the springs 420 may be tailored and customized to provide a desired axial stiffness to the plurality of surface caps 430.

In various embodiments, the spinal implant device may be fabricated using 3D printing technologies, such as laser powder bed fusion. The spinal implant device may be made from various materials approved by the FDA for spinal implants. In various embodiments, the spinal implant device is made from a titanium material or a polyetheretherketone material, among others. The spinal implant device may be made from a titanium alloy, such as a titanium niobium alloy, a titanium nickel alloy, and/or a titanium aluminum alloy, etc.

In various embodiments, the spinal implant device may be otherwise customized to have specific axial stiffness properties. For example, the spinal implant device may be manufactured such that individual sections of the device are made from specific materials, have a specific density or porosity, and/or have specific, discrete coatings or other layers (e.g., gels, etc.) that help to match the spatial hardness/stiffness of the device to the vertebral contact surface. In various embodiments, step 193 of the method 190 may include utilizing an intraoperative radiographic device to guide placement of the spinal implant device.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure.

The scope of the disclosure is accordingly to be limited by nothing other than the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

Moreover, where a phrase similar to "at least one of A, B, and C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

The steps recited in any of the method or process descriptions may be executed in any order and are not necessarily limited to the order presented. Furthermore, any reference to singular includes plural embodiments, and any reference to more than one component or step may include a singular embodiment or step. Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

Any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts or areas but not necessarily to denote the same or different materials. In some cases, reference coordinates may be specific to each figure.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A spinal implant device comprising:
   a frame, the frame comprising a tray; and
   a plurality of mechanical stiffness members extending from the tray;
   wherein each mechanical stiffness member in the plurality of mechanical stiffness members comprises a surface cap and the surface caps are porous and are configured to engage specific regions of a mapped vertebral contact surface of a vertebra of a patient.

2. The spinal implant device of claim 1, wherein an outer surface of the surface caps has a convex shape.

3. The spinal implant device of claim 1, wherein the frame defines a through-hole for bone cell ingrowth.

4. The spinal implant device of claim 1, wherein the plurality of mechanical stiffness members are formed as extensions of the frame.

5. The spinal implant device of claim 1, wherein the spinal implant device has a topography that matches the contact surface of the vertebra against which the spinal implant device is configured to be implanted.

6. The spinal implant device of claim 1, wherein the topography of the spinal implant device matches the contact surface of the vertebra against which the spinal implant device is configured to be implanted by the elevation of the plurality of mechanical stiffness members.

7. The spinal implant device of claim 1, wherein the tray is elevated relative to the frame.

8. The spinal implant device of claim 1, wherein the spinal implant device has a spatial surface structure that is tailored to accommodate the mechanical properties and structure of the vertebral contact surface of the vertebra where the spinal implant device will be implanted.

9. The spinal implant device of claim 1, wherein the spinal implant device has discrete regions with individualized mechanical properties that conform to the corresponding mechanical properties of the mapped vertebral contact surface.

10. A spinal implant device comprising: a frame comprising a tray; and a plurality of mechanical stiffness members extending from the tray wherein a first plurality of mechanical stiffness members has a first height and a second plurality of mechanical stiffness members has a second height wherein the first height and second height are different; wherein a first plurality of mechanical stiffness members has a first stiffness, and a second plurality of mechanical stiffness members has a second stiffness wherein the first stiffness and second stiffness are different and the first plurality of mechanical stiffness members and second plurality of mechanical stiffness members are configured to engage specific regions of a mapped vertebral contact surface and align with a determined mechanical property of the vertebral contact surface of a vertebra of a patient.

11. The spinal implant device of claim 10, wherein the frame further comprises a lip extending around the tray.

12. The spinal implant device of claim 10, wherein the tray comprises a non-planar surface.

13. The spinal implant device of claim 10, wherein the tray has a first height and a second height wherein the first height and the second height are different, a first plurality of mechanical stiffness members has a first stiffness and a second plurality of mechanical stiffness members has a second stiffness wherein the first stiffness and second stiffness are different, and a first plurality of surface caps on a first plurality of mechanical stiffness members with a first shape and a second plurality of surface caps on a second plurality of mechanical stiffness members with a second shape wherein the first shape and second shape are different.

14. The spinal implant device of claim 10, wherein the frame is made from a first material and the plurality of mechanical stiffness members is made from a second material wherein the first material and second material are different.

15. The spinal implant device of claim 10, wherein the frame is made from a first material having a first porosity and the plurality of mechanical stiffness members is made from a first material have a second porosity wherein the first porosity and second porosity are different.

16. The spinal implant device of claim 10, wherein a first region of the vertebra of a patient has a lower stiffness property than a second region, and the spinal implant device is configured to position the mechanical stiffness members having a lower stiffness in the first region.

17. A spinal implant device comprising: a rigid frame comprising a first side configured to directly engage a discrete, mapped site of the vertebral contact surface in a patient and proximal side; a tray; and a plurality of a mechanical stiffness members extending from the tray; wherein the plurality of a plurality of mechanical stiffness members are individually customized to provide a specific axial stiffness.

18. A spinal implant device comprising:
a rigid frame comprising a first side configured to directly engage a discrete, mapped site of the vertebral contact surface in a patient and proximal side;
a tray attached to a proximal side; and
a plurality of a mechanical stiffness members extending from the tray.

* * * * *